United States Patent [19]

Cramer

[11] 4,313,433
[45] Feb. 2, 1982

[54] ANKLE STABILIZER

[75] Inventor: Charles W. Cramer, Overland Park, Kans.

[73] Assignee: Cramer Products, Inc., Gardner, Kans.

[21] Appl. No.: 82,980

[22] Filed: Oct. 9, 1979

[51] Int. Cl.$^3$ ............................................. A61F 3/00
[52] U.S. Cl. ................................ 128/80 H; 128/166
[58] Field of Search ...................... 128/165, 166, 166.5, 128/80 H, 80 D

[56] References Cited

U.S. PATENT DOCUMENTS

| | | | |
|---|---|---|---|
| 1,027,897 | 5/1912 | Quenzer | 128/166 |
| 1,443,844 | 1/1923 | Jensen | 128/166 |
| 1,478,253 | 12/1923 | Quenzer | 128/166 |
| 1,595,087 | 8/1926 | Gibson | 128/166 |
| 2,165,879 | 7/1939 | Wilkinson | 128/166 |
| 2,645,222 | 7/1953 | Capossela | 128/166 |
| 3,028,861 | 4/1962 | Shapiro | 128/166 |
| 3,073,305 | 1/1963 | Biggs, Jr. et al. | 128/166 |
| 3,407,811 | 10/1968 | Stubbs | 128/166 |
| 3,490,450 | 1/1970 | Gardner | 128/166 |
| 3,506,000 | 4/1970 | Baker | 128/166 |
| 3,674,023 | 7/1972 | Mann | 128/166 |
| 3,970,083 | 7/1976 | Carrigan | 128/166 |
| 3,989,041 | 11/1976 | Davies | 128/166 |
| 4,084,586 | 4/1978 | Hettick | 128/165 |
| 4,085,746 | 4/1978 | Castiglia | 128/166 |
| 4,141,358 | 2/1979 | DeMarco | 128/166 |

FOREIGN PATENT DOCUMENTS

622031   4/1949   United Kingdom ............... 128/165

*Primary Examiner*—John D. Yasko
*Attorney, Agent, or Firm*—Fishburn, Gold and Litman

[57] ABSTRACT

An ankle stabilizer is provided which comprises a flexible jacket, a first strap, a second strap, a first fastener member associated with the first strap and a second fastener member associated with the second strap. The jacket snugly receives a rear portion of a foot and a lower portion of a leg associated with an ankle when the ankle stabilizer is in an operative position. The first and second straps, each have a first end thereof secured to the jacket at a location laterally centered beneath the arch of the foot. The first strap passes over the instep of the foot, wraps around the rear portion of the foot and ends on the medial or inner side of the foot, when in a stabilizing configuration. The first fastening member reusably secures the first strap in the stabilizing configuration thereof. The second strap passes over the instep of the foot, wraps around the rear of the foot and ends on the lateral or outer side of the foot, providing stabilizing support to the lateral ligaments of the foot, when in a stabilizing configuration thereof. The second fastening member reusably secures the second strap in the stabilizing configuration thereof. The jacket is constructed so as to allow stretching thereof in a horizontal direction along the foot but to permit very little stretching thereof in a vertical direction.

15 Claims, 11 Drawing Figures

ANKLE STABILIZER

BACKGROUND OF THE INVENTION

The present invention relates to a device for providing stabilizing support to an ankle to aid in preventing or minimizing the effects of an ankle injury. In particular, substantial support and stabilization is provided for the lateral ligaments of the ankle which are most often sprained or injured so as to debilitate the ankle.

Extreme twisting, flexure, or overpressure of the ankle joint often produces a debilitating injury commonly called a "sprain" which limits or prevents further use of the ankle. If the person with a previously injured ankle is participating in an athletic event, such as a basketball game, or working at a job requiring walking, it is desirable to aid that person such that they may continue to participate in or to return to the event or work as soon as possible. Therefore, the ankle has applied thereto some device to provide support and allow continued use thereof. Applying adhesive tape to injured ankles has been one conventional method of restoring utility to the ankle, but such a method is time consuming, normally requires a second party to apply the tape, and is expensive, since the tape is not reusable and must be purchased new for each use. Therefore, a preferred device is reusable and especially suitable for returning utility of the ankle to the person injured until such time as medical attention can be administered or the injury heals. The support device could, of course, be utilized for extended periods should such support be required. Most ankle "sprains" are related to injury of the outer or lateral ligaments of the ankle and, thus, it is important to provide stabilizing support to this area in particular.

In addition, because it is often desirable to get back in the sporting event or on the job with only minimal delay, it is also desirable to have a support device which can be applied easily and quickly, even by the injured person without assistance of a second party. It is also desired that the support device be worn with a shoe in place on the foot associated with the injured ankle and that the support device not be too bulky or heavy, so that same will be comfortable to the user and not bind or irritate the foot or ankle region. It is additionally desired to allow substantially free flexure motion of the foot while restricting rotating motion of the ankle.

OBJECTS OF THE INVENTION

Therefore, the principal objects of the present invention are: to provide an ankle stabilizer which can be quickly and easily applied to an injured or weak ankle and allow utilization of the ankle; to provide such a stabilizer which comprises a jacket which fits snugly about the ankle and two strap portions which wrap about the ankle to provide stabilizing support to injured or weak ligaments, especially lateral ligaments, and bones thereof; to provide such a stabilizer which is easily applied, adjustable and reusable; to provide such a stabilizer which does not require nonreusable tape; to provide such a stabilizer that may be applied and secured about an injured or weak ankle and thereafter repositioned or adjusted to provide the desired stabilization; to provide such a jacket that when applied provides substantially elastic support in a horizontal direction along the length of the foot and nonelastic support in the vertical direction; to provide such a stabilizer which is relatively light and does not hamper placement of a shoe on the foot associated with the injured or weak ankle; and to provide such an ankle stabilizer which is capable of an extended useful life, is relatively inexpensive and is particularly well adapted for the proposed use thereof.

Other objects and advantages of this invention will become apparent from the following description taken in connection with the accompanying drawings wherein are set forth, by way of illustration and example, certain embodiments of this invention.

SUMMARY OF THE INVENTION

An ankle stabilizer is provided which comprises a jacket, a first strap, a second strap, and fastening means associated with each strap. The jacket is flexible and fits snugly about an ankle region, including a lower portion of a leg and rear portion of a foot associated with the ankle, when the stabilizer is in an operative position. The jacket is elastic and allows limited stretch in a horizontal direction along the length of the foot and is substantially nonelastic in a vertical direction. The first strap is secured at one end to the jacket below the arch of the foot and has an operational configuration wherein the first strap wraps over the instep of the foot, around the rear portion of the foot, and ends on the medial or inner side of the foot approximately midway between the top and bottom thereof. The second strap is also secured at one end to the jacket below the arch of the foot and has an operational configuration wherein the second strap wraps sequentially over the instep of the foot, around the rear of the foot above the heel thereof, substantially over the lateral or outer ligaments along the outside of the foot, and ends on the outside of the foot approximately midway between the top and bottom thereof. Fastening means secure the strap associated therewith in the respective operational configuration thereof.

The drawings constitute a part of this specification and include exemplary embodiments of the present invention and illustrate various objects and features thereof.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates an embodiment of an ankle stabilizer according to the present invention which is illustrated in FIGS. 1 through 6 and is for use on a right ankle region. The ankle stabilizer 1 comprises an elongate flexible member 2 secured near the middle thereof to a sleeve or jacket 3 adapted for being snugly or tightly received around the ankle region including an associated rear portion of a foot and a lower portion of a leg of a human.

Figure 6:
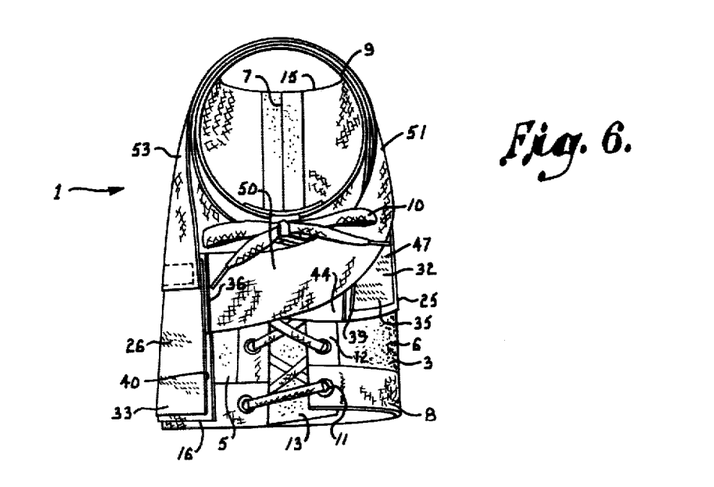
FIG. 6 is a top plan view of the ankle stabilizer as shown in FIG. 5.

As used herein, the term "front" means in the direction of the bottom of the page with respect to the view of the stabilizer seen in FIG. 6 (that is, toward the toe of a foot when the stabilizer is being worn) and the term "rear" has the opposite meaning. The terms "upper", "lower", "horizontal", "vertical", and other common derivatives thereof have the same meaning as shown in the drawings.

The jacket 3 is preferably formed of suitable sheet material shaped to be secured to and enclose the ankle area of a foot. In the illustrated structure the jacket 3 comprises a fabric material which is elastic in a horizontal direction or along the foot and is substantially nonelastic in a vertical direction, that is around the foot and between the ankle region and heel. Thus, the jacket 3 provides substantially elastic support or stabilization in a horizontal direction along the foot and substantially inelastic support or stabilization in a vertical direction around the foot and between the ankle region and heel of the foot. The jacket 3 includes a rear panel, portion or section 4, a lateral or outer side panel, portion or section 5 and a medial or inner side panel, portion or section 6. The ankle stabilizer 1 has an operative position wherein the jacket 3 is snugly located about the ankle region of a foot. When the stabilizer is in the operative position, the jacket rear section 4 wraps around a rearward portion of the leg between the heel and a location above the lateral and medial mallelouses of the Fibula and Tibia bones respectively. Also, when the ankle stabilizer 1 is in the operative position, the jacket outer side section 5 merges with and extends forward of the rear section 4 approximately half way along the length of the foot and extends from beneath the foot along the outer side thereof to the top or instep of the foot. Again, when the ankle stabilizer 1 is in the operative position, the inner side section 6 merges with and extends frontwardly of the rear section 4 substantially as a mirror image of the outer side section 5 except that the outer side section 5 extends slightly forward, in the nature of about ¼ to 1 inch, of the inner side section 6 near the top of each side section 5 and 6. The outer side section 5 front edge tapering rearward from the top down so as to join flushly with the front bottom corner of the inner side section 6. The outer side section 5 and inner side section 6 are joined at lower edges thereof along a juncture 7 by suitable means, such as stitching or the like. A front reinforcing strap or binding 8 extends entirely around a front edge of the jacket 3 and is secured thereto by stitching or the like. A top reinforcing strip or binding 9 extends around the upper leg encircling portion of the jacket 3 and is secured thereto by suitable means such as stitching or the like. The outer side section 5 and inner side section 6 are interconnected by securing means along a top edge thereof, such as by lacings 10 received through lacing apertures or grommets 11 located near the upper edge of both the outer side section 5 and inner side section 6. A tongue 13 extends between the outer side section 5 and the inner side section 6 below the lacings 10 so as to protect the foot from the lacings 10 and also aid in providing a better fit for snugness. The tongue 13 is tacked or otherwise secured along a front portion of an edge 14 thereof to the inner side section 6. The tongue 13 is an optional part of the jacket 3 and can be removed should the user thereof desire less thickness and bulk in the jacket 3. Preferably, the jacket rear section 4 does not extend over the heel of the foot, thus defining an open or cut out bottom rear portion 15 of the jacket 3 through which the heel extends when the support 1 is in the operative position. The cutout portion 15 can be enlarged to accomodate larger heels or to allow the stabilizer 1 to shift slightly forward on the foot. Positioned on the outer surface near the upper front of the outer side section 5 is a reusable fabric fastener member 16 secured to the outer side section 5 by stitching or the like. The fabric fastener member 16 comprises a portion of a hook and loop fastener such as is sold under the trademark "Velcro" or the like. The fabric fastener member 16 will be discussed further hereinafter.

The flexible member 2 may be a single unit as shown or may be comprised of multiple individual units or straps. The flexible member 2 preferably is a thin flat strong fabric band or the like and is secured by suitable means, such as stitching or the like, to the outer surface of the jacket 3 beneath the sole or plantar portion of the foot when the support 1 is in the operative position. The flexible member 2 is longitudinally located beneath the arch of the foot, preferably near the front side of the calcaneum bone when the support 1 is in the operative position and laterally attached near or at the juncture 7 of the jacket inner side section 6 and outer side section 5.

Figure 1:
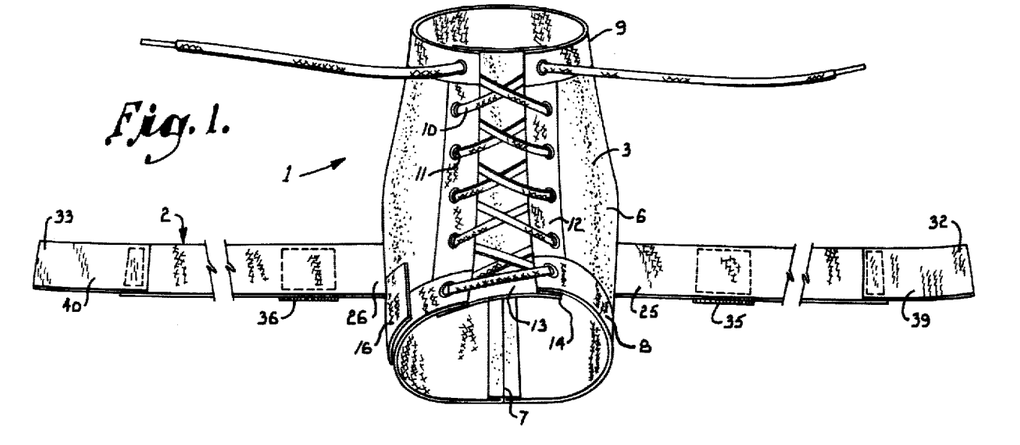
FIG. 1 is a perspective view of a right foot ankle stabilizer embodying the present invention comprising a jacket, a first strap an a second strap, both straps being shown in a nonstabilizing configuration.

Before attachment to the jacket 3, the flexible member 2 is twisted so as to produce a fold 22 near the attachment thereof to the jacket 3. Opposite portions of the flexible member 2 not attached to the jacket define a first strap 25 and a second strap 26. The straps 25 and 26 have respective attached ends 28 and 29 secured to the jacket 3 and respective free or distal ends 32 and 33. Each of the straps 25 and 26 has an operational configuration which will be discussed hereinafter and a nonoperational configuration wherein each of the straps 25 and 26 is loose and free of the jacket 3, as illustrated in FIG. 1, such that the support 1 can be placed in or removed from the operational position thereof on the ankle region of the user without interference from the straps 25 and 26.

The fold 22 in the flexible member 2 is such that the straps 25 and 26 diagonally overlap near the attachment of the flexible member 2 to the jacket 3 in such a manner that the straps 25 and 26 extend outwardly from the interconnection thereof at an angle with respect to one another when the straps 25 and 26 are in the non-operative configuration respectively and are laid out straight in a horizontal plane. Preferably when so horizontally laid out, the distal ends 32 and 33 of the straps 25 and 26 respectively are forward of the attached ends 28 and 29 thereof, such that the straps 25 and 26 can be more easily positioned in the operative configuration thereof, since each strap 25 and 26 must extend over the instep of the foot slightly forward of the attachment 21 of the flexible member 2 to the jacket, when in such an operative configuration. Preferably each of the straps 25 and 26 when placed in the horizontal plane above discussed, are at an angle in the nature of 20° with respect to a transverse horizontal line extending through the fold 22.

Figure 5:
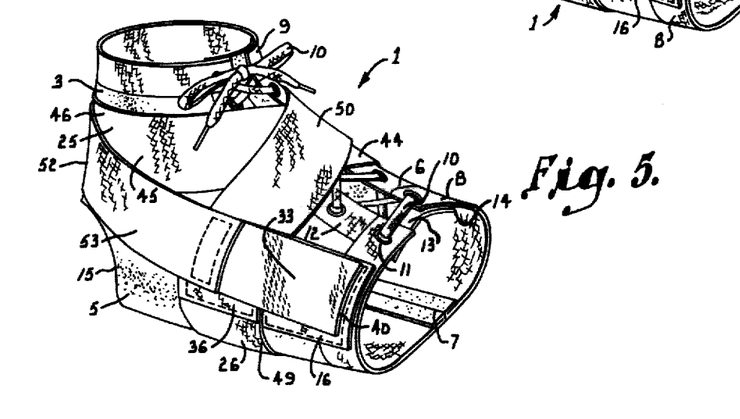
FIG. 5 is a perspective view of the ankle stabilizer in a completely applied position with both first and second straps in the respective stabilizing configurations thereof.

Positioned intermediately along the straps 25 and 26 are first fastener portions or members 35 and 36 respectively. The first fastener member 35 is located along the strap 25 such that when the strap 25 is in the operative configuration, the member 35 will be on the outer side thereof and on the inner side of the foot. The first fastener member 36 is located along the strap 26 such that when the strap 26 is in the operative configuration, the member 36 will be on the outer side thereof and on the lateral or outer side of the foot forward of the lateral ligaments associated with the foot and ankle and adjacent to or alongside the fastener 16. The straps 25 and 26 also include second fastener portions or members 39 and 40 respectively, located near the associated distal ends 32 and 33 thereof. The second fastener members 39 and 40 are also located so as to mate with the first fastener members 35 and 36 respectively when the straps 25 and 26 are in the operational configuration thereof; thus each of the strap distal ends 32 and 33 is secured to an intermediate portion of the strap associated therewith when the straps are in an operational configuration, as is illustrated in FIGS. 5 and 6. In addition, the second fastener member 40 on strap 26 also mates with the fastener member 16 on the jacket 3. Each of the first fastener members 35 and 36 and second fastener members 39 and 40 is preferably a reusable and adjustable fabric fastener, such as the illustrated hook and loop fasteners marketed under the trademark "Velcro", snaps, or the like. In order to reduce bulk and for custom fitting, excess portions of the second fastener members 39 and 40 may be trimmed therefrom when the straps 25 and 26 are in operational configurations thereof. The first fastener members 35 and 36 may comprise either segment of the hook and loop fastener with the second fastener members 39 and 40 being the opposite segment. The fastener members 35, 36, 39 and 40, may be secured to the surface of the straps 25 and 26 by suitable means such as stitching, gluing, or may be integrally included in the straps 25 and 26, as is illustrated, thus reducing thickness and weight of the straps 25 and 26. Preferably the fastener members 39 and 40 are attached to the ends of the straps 25 and 26 respectively without the strap material extending under the members 39 and 40 over a major surface thereof. As is illustrated, the fastener members 39 and 40 are relatively thin and of sufficient length, so that when mated with the fasteners 35 and 36 respectively, they extend over or cover same.

The straps 25 and 26 preferably have a uniform width sufficient to prevent gouging and digging thereof into the skin of the user. The straps 25 and 26 are constructed of strong flexible material such as canvas, highly flexible woven cloth, pliable plastic, combinations of such materials, or the like and are preferably lightweight, relatively thin and substantially nonelastic.

As was previously discussed, the straps 25 and 26 have respective operational configurations, wherein they are in position to provide stability to the ankle region. For the straps 25 and 26 to be in the respective operational configuration thereof, the stabilizer 1 must be in the operative position wherein the jacket 3 is snugly positioned about the ankle region to be stabilized thereby.

Figure 2:
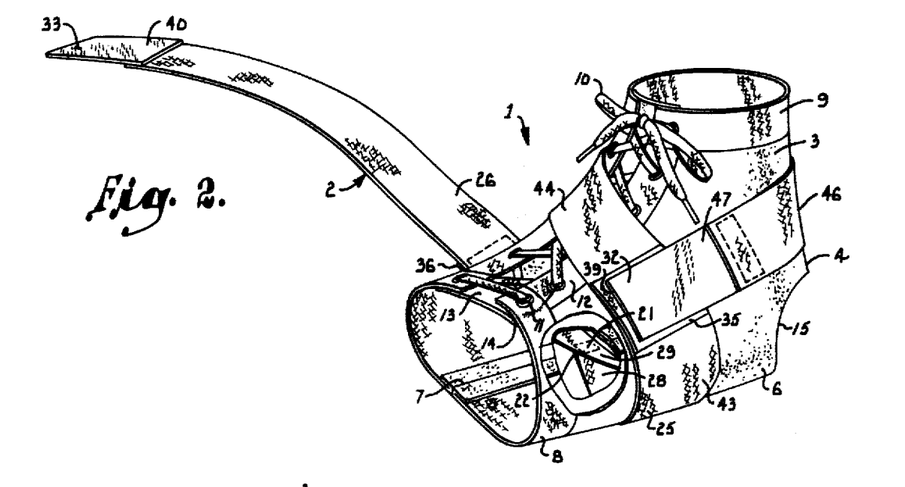
FIG. 2 is a perspective view of the ankle stabilizer showing the first strap in a stabilizing configuration.
Figure 3:
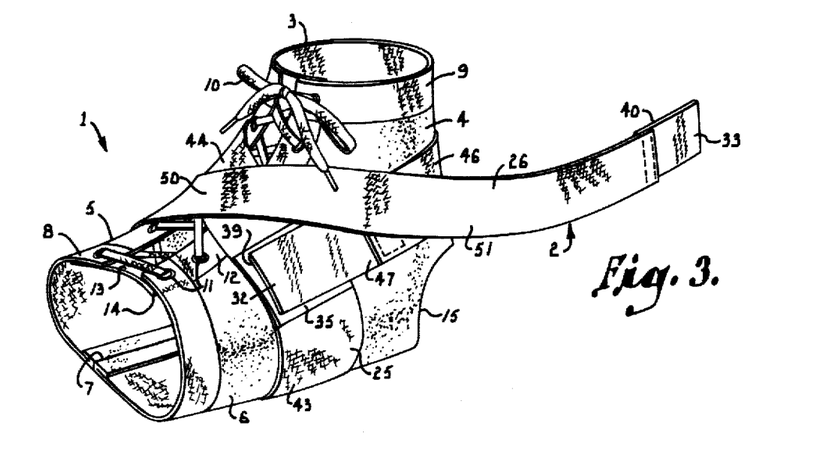
FIG. 3 is a perspective view of the ankle stabilizer showing the first strap in the stabilizing configuration thereof and the second strap in a partial stabilizing configuration thereof.
Figure 4:
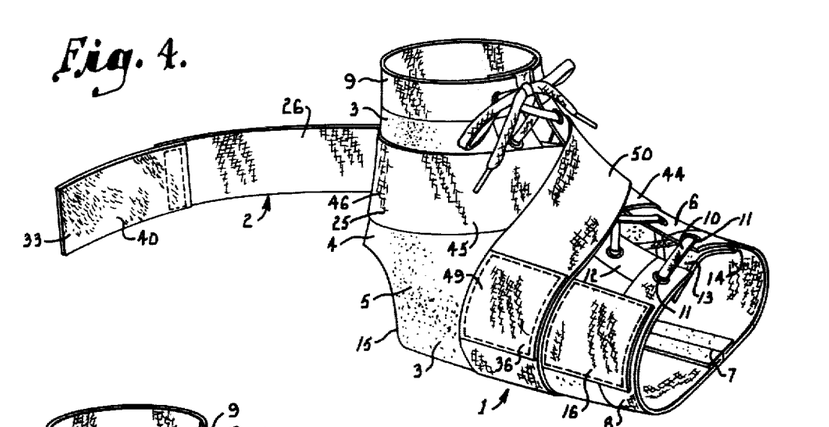
FIG. 4 is another perspective view of the ankle stabilizer with the straps in similar position and from the opposite side to that shown in FIG. 3.

The operational configuration of the first strap 25 of the embodiment illustrated in FIGS. 1 through 6, is best seen in FIG. 2. When in the operational configuration, the strap 25 has a medial rise portion 43 extending between the attached end 28 thereof and the upper part or instep of the foot on the medial or inner side of the jacket 3, an instep portion 44 extending over the instep of the foot, a lateral rearward portion 45 (see FIG. 4) extending from near the top of the foot to near the back of the leg above the heel or in the region of the Achilles tendon, a rear portion 46 wrapping about the rear of the leg above the heel, and a medial forward portion 47 extending from the rear of the leg and ending approximately midway between the sole and instep of the foot on the medial or inner side thereof. The instep portion 44 of the strap 25 is slightly forward of the attached end 28 thereof; attainment of this forward position is facilitated by the strap 25 being slightly angled forward near the distal end 32 with respect to the opposite end 28 thereof as was previously discussed. The strap 25 fits tightly or snugly about the ankle region and is secured in the operational configuration by fastening means comprising the fastening members 35 and 39.

The operational configuration of the second strap 26 of the embodiment illustrated in FIGS. 1 through 6 is best seen in FIGS. 5 and 6. FIGS. 2, 3, 4 and 5 illustrate sequential placement of the second strap 26 in the operational configuration thereof. When in the operational configuration, the second strap 26 has a lateral rise portion 49 extending between the attached end 29 thereof and the upper part or instep of the foot on the outer side of the jacket 3, an instep portion 50 extending over the top of the foot and crossing over the instep portion 44 of the strap 25, a medial rearward portion 51 extending from near the top of the foot to near the back of the leg above the heel thereof or in the region of the Achilles tendon, a rear portion 52 wrapping about the rear of the leg above the heel and crossing over the rear portion 46 of the strap 25, and a lateral forward portion 53 extending from the rear of the leg and ending approximately midway between the sole of the foot and top of the instep of the foot on the lateral or outer side thereof. Preferably, when in the operational configuration, the distal end 33 of the second strap 26 is positioned lower than the rear portion 52 thereof, such that the lateral forward portion 53 thereof slopes downwardly from the rear of the foot to the second strap distal end 33. The second strap 26 fits tightly or snugly about the ankle region and is secured in operational configuration by fastening means comprising the fastening members 16, 36 and 40. Preferably, the second strap 26 extends forwardly of the first strap 25 and extends at least forwardly of the lateral ligament of the ankle when in the operational configuration. The position of the distal end of the second strap 26 and the angle of the lateral forward portion 53 thereof tend to control the degree of restrictive stability obtained by the stabilizer 1.

In terms of anatomy, the bones of the leg are joined to the bones of the foot in the region of the ankle by various ligaments which can be divided into two fairly broad catagories, and in particular: the medial or inner side of the foot ligaments and the lateral or outer side of the foot ligaments. Basically, the medial ligaments connect the Tibia and Talus bones and comprises the deltoid ligament, a very strong triangular band. Also basically, the lateral ligaments interconnect the Fibula and the Talus bones and comprise the calcaneofibular ligament, the anterior talofibular ligament and the posterior talofibular ligament. The lateral ligaments are substantially weaker in comparision to the medial ligaments and normally sustain the debilitating injury when the ankle is "sprained". In the embodiment illustrated in FIGS. 1 through 6, the first strap 25 and, more importantly, the second strap 26 both extend (see lateral portions 45 and 53 respectively) over a substantial portion of the lateral ligaments when in the respective operational configurations thereof and provide support or restrictive stability to these ligaments and also tend to hold the ankle bones of this region in proper position. The embodiment of FIGS. 1 through 6 also provides support or stabilization for the medial ligaments (see medial portion 47 of strap 25 and medial portion 51 of strap 26) as the straps 25 and 26 both extend over a substantial portion of the medial ligaments providing restrictive stability to same and tending to hold the ankle bones of this region in the proper position thereof.

Although the embodiment shown in FIGS. 1 through 6 is for a right ankle region, the stabilizer 1 may be produced as a mirror image of the embodiment shown for use on the left ankle region.

In use, the ankle stabilizer 1 of the embodiment in FIGS. 1 through 6 is designed to provide support and stabilization for an injured or weak ankle such that the user of the stabilizer 1 can make immediate use of his ankle for work or play. The stabilizer 1 is utilized by removing the shoe associated with an injured or weak ankle and placing the jacket 3 about the ankle region normally leaving the sock of the user in place beneath the jacket 3. The lacings 10 of the jacket 3 are tightened such that the jacket 3 fits snugly about the ankle region at which time the stabilizer 1 is substantially in the operative position. Minor changes in the positioning of the stabilizer 1 may be accomplished by slightly enlarging the opening 15. The first strap 25 is then wrapped tightly about the foot and secured in the operational configuration thereof by mating fastener members 35 and 39, as is illustrated in FIGS. 3 through 6 and described hereinabove. Thereafter, the second strap 26 is wrapped tightly about the foot and secured in the operational configuration thereof by mating fastener member 40 with fastener members 16 and 36, as is illustrated in FIGS. 2 through 5 and described hereinabove to provide desired restrictive stability. The user then replaces his shoe over the stabilizer 1. The stabilizer 1 may be applied to the ankle by the user himself or with the aid of a second party. To remove the stabilizer 1, the above procedure is reversed.

Figure 7:
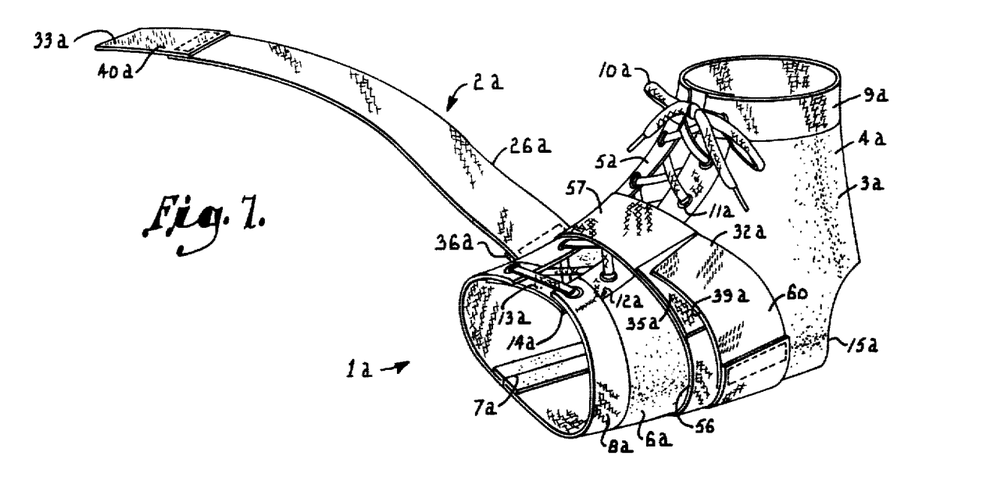
FIG. 7 is a perspective view of a modified ankle stabilizer for a right foot having a jacket, a first strap and a second strap, showing the first strap in a stabilizing configuration thereof.
Figure 8:
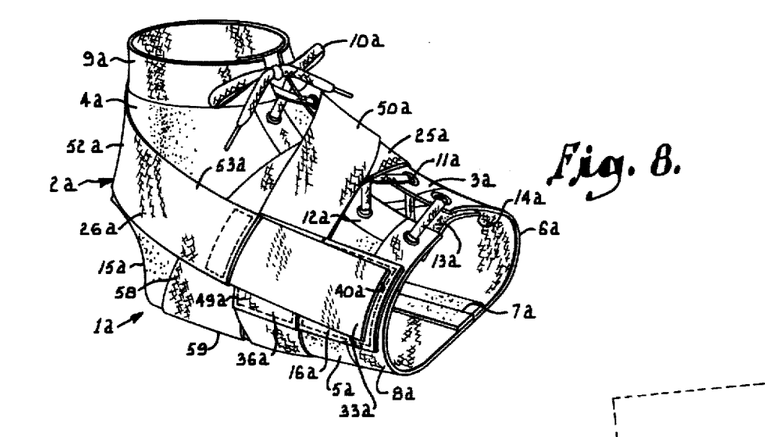
FIG. 8 is a perspective view of the ankle stabilizer of FIG. 7 showing the first strap and the second strap in stabilizing configurations thereof.

The reference numeral 1a generally represents a second modified embodiment of the ankle support or stabilizer of the present invention having a modified operational configuration of the first strap 25a. Since the ankle stabilizer 1a is otherwise substantially the same as the previously described device, similar parts appearing in FIGS. 7 and 8 illustrating the second embodiment and FIGS. 1 through 6 illustrating the first embodiment respectively, are represented by the same, corresponding reference numerals except for the addition of the suffix "a" to the numerals of the modified device. When the first strap 25a of the modified embodiment is in an operational configuration thereof, the first strap 25a comprises in sequence a first medial rise portion 56 extending from the bottom of the foot to the top of the foot on the medial or inner side thereof, an instep portion 57 extending over the top of the instep of the foot, a lateral downward portion 58 extending between the top of the foot and the bottom of the foot on the lateral or outer side thereof, an underfoot portion 59 extending laterally beneath the foot, and a second medial rise portion 60 positioned partially rearward of the first medial rise portion 56 and ending approximately midway between the bottom and top of the foot on the medial or inner side thereof.

The second embodiment illustrated in FIGS. 7 and 8 is for use with a right ankle region and is utilized substantially as previously described for the first embodiment except that the first strap 25a is wrapped according to the operational configuration described therefor. This embodiment provides additional stabilization for the ligaments and bones associated with the arch of the foot.

Figure 9:
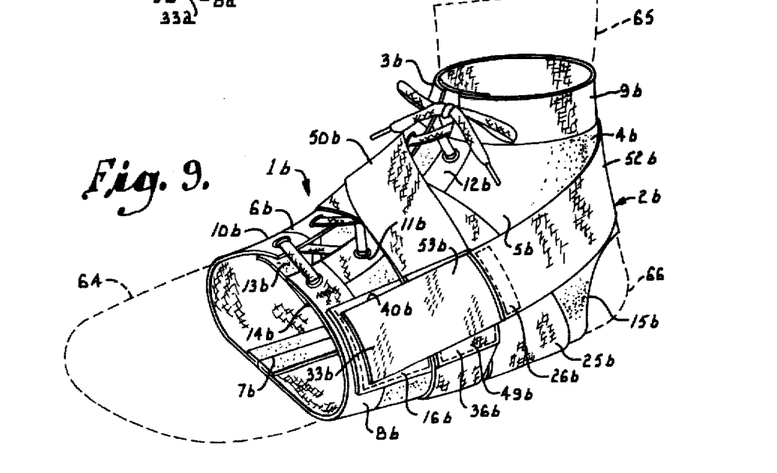
FIG. 9 is a perspective view of the modified ankle stabilizer of FIG. 7 for a left foot showing the stabilizer positioned on a human ankle region and both first and second straps in respective stabilizing configurations.

The reference numeral 1b (see FIG. 9) generally represents a left foot version of the second modified embodiment of the invention illustrated in FIGS. 7 and 8. The embodiment of FIG. 9 is essentially a mirror image of the embodiment of FIG. 8, and similar parts appearing in FIG. 9 have the same corresponding reference numeral as those appearing in FIG. 7 except that the suffix "a" is replaced with the suffix "b". A foot 64 with an associated leg 65 and heel 66 are shown in phanthom in FIG. 9 with the stabilizer 1b in an operative position thereon and with the straps 25b and 26b in an operational configuration thereabout.

Figure 10:
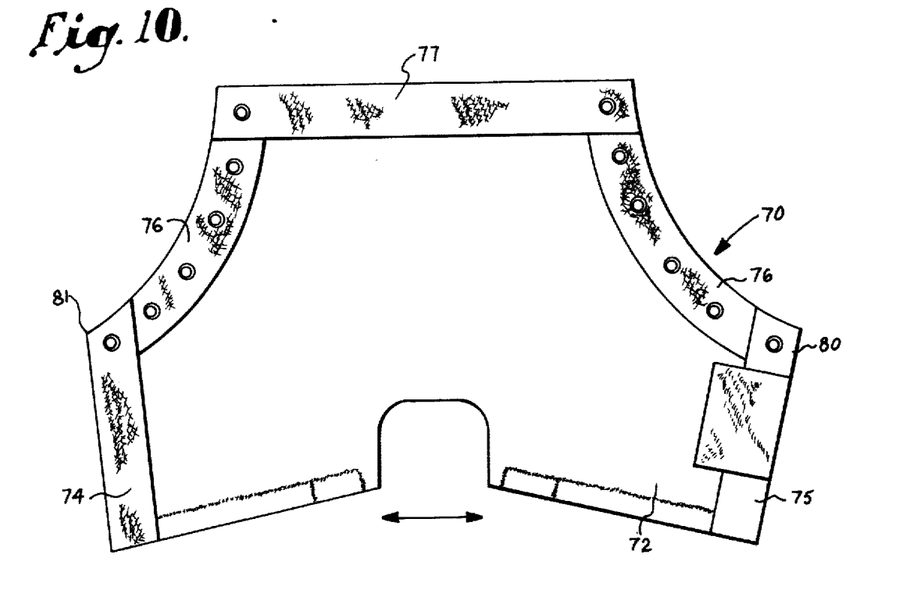
FIG. 10 is an outside view of a portion of a jacket during construction.
Figure 11:
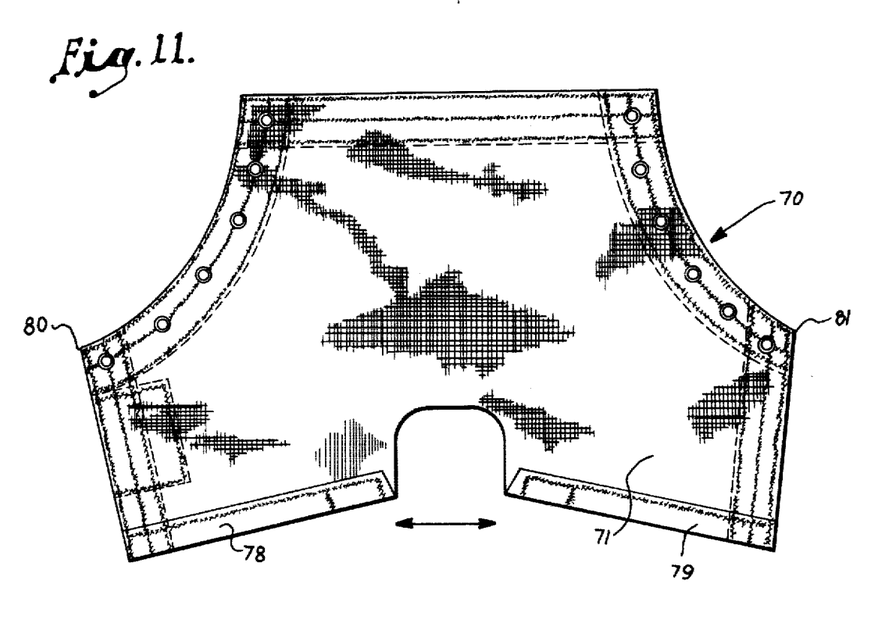
FIG. 11 is an inside view of a portion of the jacket of FIG. 10 during construction.

The jackets 3, 3a and 3b of each of the previously described embodiments are constructed in a similar manner. An intermediate stage of the jacket construction is illustrated in FIGS. 10 and 11 wherein a sheet or web 70 of jacket material is shown just prior to final completion of a jacket. The web 70 has an inner or foot engaging surface 71 (that is, surface 71 engages the foot when the completed jacket is placed thereon), shown in FIG. 11, and an outer shoe engaging surface 72, shown in FIG. 10. The web 71 preferably comprises a laminate consisting of a poly vinyl chloride outer surface 72 and a fabric inner surface, such as is marketed under the trademark "Naugahyde" by Uniroyal, Inc. The web 70 should be flexible, resilient and tough and preferably has particular elastic properties. That is, the web 70 should be moderately elastic in a horizontal direction as indicated by the arrows in FIGS. 10 and 11, such that when formed into a completed jacket and placed on a foot, the web 70 will be elastic along the length of the foot and will provide restrictive elastic support in such a direction. In addition, the web 70 should be substantially unelastic in a vertical direction as seen in FIGS. 10 and 11, such that when formed into a completed jacket and placed on a foot, the web 70 will be substantially inelastic between the sole of the foot heel and the ankle region and around the foot where the completed jacket will wrap around the foot arch and instep. The particular elastic properties of the preferred web 70, thus described provide stable vertical support to a foot from a completed jacket while allowing some horizontal movement along the foot and, thus, improving the comfort of a user.

The web 70 illustrated in FIGS. 10 and 11 has reinforcing bindings 74, 75, 76 and 77 attached by stitching around edges thereof. The bindings 74 and 75 are joined at the bottom thereof in a completed jacket to form a front reinforcing binding such as 8 in FIG. 1. Lower edges 78 and 79 of the web 70 are turned inwardly and tacked to provide additional strength. The lower edges 78 and 79 are joined together in a completed jacket to form a juncture such as 7 in FIG. 1. The bindings 76 and 77 somewhat limit the stretching which can occur in the web 70 and prevent same from becoming loose in cooperation with the lacings 10.

The web 70 is slightly asymetrical about an imaginary vertical axis passing through the middle of FIGS. 10 or 11. In particular with reference to FIG. 10, a far right hand edge 80 of the web 70 at the top thereof extends further from such an imaginary axis than a top of a far left hand edge 81 of the web 70. Such an asymetrical design allows the lateral or outside side section of a completed jacket to extend slightly forward of the opposite side section which has been found to improve the comfort of a user.

It is to be understood that while certain embodiments of the present invention have been described and shown herein, it is not to be limited to specific forms or arrangement of parts herein described and shown.

Having thus described the invention, what is claimed and desired to secure by Letters Patent is:

1. A stabilizer for a human ankle comprising:
   (a) a jacket adapted for snugly positioning about a rear portion of a foot and lower portion of a leg associated with the ankle;
   (b) first and second straps having first ends respectively attached to said jacket;
   (c) said first strap having an operational configuration wherein same wraps about a rear portion of the foot when said stabilizer is in the operative position and has a second end located on the medial side of the foot approximately midway between the sole and instep of the foot;
   (d) said second strap having an operational configuration wherein starting from the first end thereof same wraps sequentially up the lateral side of the foot, over the instep of the foot, around the rear of the foot above the heel thereof, and along the lateral side of the foot substantially over the lateral ligaments associated therewith; said second strap ending on the lateral side of the foot approximately midway between the sole and instep of the foot; and
   (e) reusable first and second fastening means located on the medial and lateral sides of the foot respectively when said first and second straps are in the operational configuration thereof approximately midway between the sole and the instep of the foot for securely connecting said first and second straps in the respective configuration thereof.

2. The stabilizer according to claim 1 wherein:
   (a) said first strap in the operational configuration thereof wraps sequentially up the medial side of the foot, over the instep of the foot, around the rear of the foot above the heel thereof, being crossed thereat by said second strap, and along the medial side of the foot substantially over the medial ligaments associated therewith.

3. The stabilizer according to claim 1 wherein:
   (a) said first strap in the operational configuration thereof wraps sequentially up the medial side of the foot, over the instep of the foot, down the lateral side of the foot, around the sole of the heel of the foot spaced rearwardly of the location whereat said flexible members are secured to said jacket, and upwardly toward the instep of the foot along the medial side thereof.

4. The stabilizer according to claim 1 wherein:
   (a) said second fastening means comprises first and second members of a hook and loop fabric fastener.

5. The stabilizer according to claim 4 wherein:
   (a) said second strap includes a first portion of said fabric fastener first member secured to and located inbetween the ends thereof and positioned such that said first portion is on the outer side of the first strap and approximately between the instep and sole of the foot when said second strap is in the operational configuration associated therewith;
   (b) said jacket includes a second portion of said fabric fastener first member secured thereto and positioned adjacent to and frontwards of said first portion when said second strap is in the operational configuration associated therewith; and
   (c) said fabric fastener second member is fixedly attached to a distal end of said second strap; whereby the distal end of said second strap is fastened to both itself and said jacket when said first and second fabric fastener members are mated.

6. The stabilizer according to claim 5 wherein:
   (a) said first fastening means comprises first and second members of a hook and loop fabric fastener; said first fastening means first member being attached to the first strap inbetween the ends thereof; said first fastening means second member being attached to a distal end of said strap; said first fastening means first and second member mating when said first strap is in the operational configuration thereof.

7. In an ankle stabilizer comprising: a flexible jacket adapted for positioning around the ankle region including the rear of the foot and lower leg of a human and including means for adjusting tightness of the jacket about the ankle region; said stabilizer having an operative position on the ankle; the improvement comprising:
   (a) an elongate strap having a first end secured to said jacket beneath the sole of the foot and longitudinally located beneath the arch of the foot when said stabilizer is in the operative position thereof; and wherein
   (b) said strap has an operational configuration wherein starting from said first end said strap wraps sequentially up the lateral side of the foot, over the top of the foot, around the lower leg above the heel associated therewith, and along the lateral side of the foot so as to provide stabilization to lateral ligaments associated with the ankle; said strap having a second end securely connected to said jacket frontward of said lateral ligaments when said strap is in the operational configuration thereof; and (c) fastening means located approximately midway between the sole and instep of the foot and securing said strap second end to said jacket when said strap is in the operational configuration thereof.

8. The stabilizer according to claim 7 wherein said strap comprises a first strap and including:

(a) a second strap attached at a first end thereof to said first strap first end; and (b) said second strap having an operational configuration wherein same wraps about the rear of the foot and has a second end thereof securely connected to said jacket between the instep and sole of the medial side of the foot.

9. An ankle stabilizer comprising:

(a) a jacket adapted for being snugly received on an ankle region including a rear portion of a foot and a lower leg of a human and having a lacing for tightening said jacket about the ankle region; said stabilizer having an operative position such that said jacket is located about the ankle region;

(b) a first flexible strap secured at a first end thereof to said jacket at a location beneath the planter surface of the foot when said stabilizer is in the operative position thereof; said first strap having an operative configuration associated with the operative position of the stabilizer wherein said first strap extends from said first strap first end beneath the foot up the medial side of the foot, over the instep of the foot, around the rear portion of the foot, and over the medial side of the foot to a location inbetween the instep and sole of the foot;

(c) first reusable fastening means for tightly securing said first strap in the operative configuration thereof, wherein a distal end of said first strap is secured to an intermediate location along said second strap; said first fastening means being positioned approximately inbetween the instep an sole of the foot on the medial side of the foot when said first strap is in the operative configuration thereof;

(d) a second elongate flexible strap secured at a first end thereof to said jacket at a location beneath the plantar surfate of the foot when said jacket is in the operative position thereof; said second strap having an operational configuration associated with the operative position of the stabilizer wherein said second strap extends sequentially from said first strap first end beneath the foot up the lateral side of the foot, over the instep of the foot, around the rear of the foot above and adjacent to the heel thereof, and frontwardly along the lateral side of the foot; said first strap providing stabilization for lateral ligaments associated with the ankle; and (e) second reusable fastening means for tightly securing said second strap in the operative configuration thereof, wherein a distal end of said second strap is secured to an intermediate location along said second strap and to said jacket; said second fastening means being positioned approximately inbetween the instep and sole of the foot on the lateral side of the foot when said second strap is in the operative configuration thereof.

10. The stabilizer according to claim 9 wherein:

(a) the distal end of said second strap when in the operative configuration thereof is secured to both said intermediate location on said second strap and to said jacket at adjacent positions on the lateral side of the foot forward of the lateral ligaments and inbetween the instep and sole of the foot.

11. The stabilizer according to claim 9 wherein:

(a) each of said first and second fastening means comprise first and second portions of hook and loop fabric fasteners respectively;

(b) said first fabric fastener portions being attached to the distal ends of said first and second straps respectively;

(c) said first and second portions of each respective fastener having a mating thickness at least as thin as said straps; whereby said first and second portions of each respective fastener do not bulge above the strap associated therewith when mated.

12. The stabilizer according to claim 9 wherein:

(a) said jacket includes a lateral side section and a medial side section; each said side section having a front edge;

(b) said lateral side section edge at the top thereof extending forward of said medial side section edge, thereby improving comfort of a user of said stabilizer.

13. The stabilizer according to claims 1, 7 or 9 wherein:

(a) said jacket comprises a web for wrapping about the ankle region including a rear portion of an associated foot and a lower portion of an associated leg of a user; said web being held snugly in place by securing means;

(b) said web having elastic properties such that said web when placed about the foot is substantially inelastic in a vertical direction around the foot and between the ankle region and a sole of an associated heel of the foot; said web also being moderately elastic in a horizontal direction along the length of the foot.

14. The jacket according to claim 13 wherein:

(a) said web is constructed of vinyl and fabric laminated together; said vinyl comprising an outer surface of said web when in place on the foot and said fabric being substantially inelastic in one direction and comprising an inner foot engaging surface of said web when in place on a foot.

15. A stabilizer for a human ankle comprising:

(a) a jacket adapted for snugly positioning about a rear portion of a foot and lower portion of a leg associated with the ankle;

(b) at least one elongate flexible member secured at a medial position therealong to said jacket on the plantar side of said foot when said stabilizer is in an operative position on the ankle; said flexible member defining first and second straps having first ends respectively attached to said jacket;

(c) said first strap having an operational configuration wherein same wraps about a rear portion of the foot when said stabilizer is in the operative position and has a second end located on the medial side of the foot approximately midway between the sole and instep of the foot;

(d) said second strap having an operational configuration wherein starting from the first end thereof same wraps sequentially up the lateral side of the foot, over the instep of the foot, around the rear of the foot above the heel thereof, and along the lateral side of the foot substantially over the lateral ligaments associated therewith; said second strap ending on the lateral side of the foot approximately midway between the sole and instep of the foot; said (e) reusable first and second fastening means for securely connecting said first and second straps in the respective operational configuration thereof; and wherein:

(f) said flexible member is twisted such that said first and second straps diagonally overlap one another at the location whereat said flexible member is secured to said jacket, such that when said first and second straps are placed in a horizontal plane, respective distal ends thereof extend frontwardly of the location whereat said flexible member is secured to said jacket.

* * * * *